United States Patent
Griffin

(10) Patent No.: US 12,310,656 B2
(45) Date of Patent: May 27, 2025

(54) OPTICAL FIBER DEVICE WITH SPATIALLY SELECTABLE OUTPUT

(71) Applicant: Cyclone Biosciences, LLC, Phoenix, AZ (US)

(72) Inventor: Stephen E. Griffin, Peoria, AZ (US)

(73) Assignee: CYCLONE BIOSCIENCES, LLC, Phoenix, AZ (US)

(*) Notice: Subject to any disclaimer, the term of this patent is extended or adjusted under 35 U.S.C. 154(b) by 0 days.

(21) Appl. No.: 18/505,453

(22) Filed: Nov. 9, 2023

(65) Prior Publication Data

US 2024/0081908 A1     Mar. 14, 2024

Related U.S. Application Data

(63) Continuation-in-part of application No. 18/242,960, filed on Sep. 6, 2023, now abandoned, which is a continuation-in-part of application No. 18/228,983, filed on Aug. 1, 2023.

(60) Provisional application No. 63/425,472, filed on Nov. 15, 2022, provisional application No. 63/414,974, filed on Oct. 11, 2022, provisional application No. 63/405,984, filed on Sep. 13, 2022.

(51) Int. Cl.
| | |
|---|---|
| A61B 18/22 | (2006.01) |
| A61B 17/00 | (2006.01) |
| A61B 18/00 | (2006.01) |
| A61B 18/20 | (2006.01) |
| A61B 90/00 | (2016.01) |
| A61N 5/06 | (2006.01) |

(52) U.S. Cl.
CPC .... *A61B 18/22* (2013.01); *A61B 2017/00907* (2013.01); *A61B 2018/00196* (2013.01); *A61B 2018/20553* (2017.05); *A61B 2018/205545* (2017.05); *A61B 2018/2205* (2013.01); *A61B 2018/2266* (2013.01); *A61B 2018/2272* (2013.01); *A61B 2090/034* (2016.02); *A61N 2005/063* (2013.01)

(58) Field of Classification Search
CPC .......... A61B 18/22; A61B 2018/2205; A61B 2018/2266; A61B 2018/2272; A61B 2090/034; A61B 18/201; A61B 2018/2015; A61B 2018/2035; A61B 2018/20553; A61B 2018/205545; A61B 2018/205547
USPC ...................................... 606/15–18
See application file for complete search history.

(56) References Cited

U.S. PATENT DOCUMENTS

| | | | |
|---|---|---|---|
| 5,428,699 A | 6/1995 | Pon | |
| 5,537,499 A | 7/1996 | Brekke | |
| 5,562,657 A | 10/1996 | Griffin | |
| 6,120,498 A * | 9/2000 | Jani | A61F 9/00802 606/4 |
| 6,163,641 A * | 12/2000 | Eastgate | G02B 6/032 385/125 |
| 9,323,005 B1 | 4/2016 | Griffin | |
| 9,421,065 B2 * | 8/2016 | Splinter | A61B 18/24 |
| 9,488,782 B2 | 11/2016 | Griffin | |

(Continued)

*Primary Examiner* — Ahmed M Farah
(74) *Attorney, Agent, or Firm* — Quarles & Brady LLP; Yakov S. Sidorin

(57) ABSTRACT

An optical-fiber-based optical switch arrangement configured to redirect light from axial propagation to off-axis propagation due to axial repositioning of the optical fiber within the optical termination element and internally reflecting light in an annular fashion off the axis in one state of the switch arrangement and not in the other.

23 Claims, 6 Drawing Sheets

(56) References Cited

U.S. PATENT DOCUMENTS

| | | |
|---|---|---|
| 11,097,395 B2 | 8/2021 | Griffin et al. |
| 11,826,097 B2 * | 11/2023 | Griffin .................. A61B 18/22 |
| 2010/0016842 A1 * | 1/2010 | Fix ....................... A61B 18/245 |
| | | 606/14 |
| 2021/0330383 A1 * | 10/2021 | Griffin ................ A61N 5/0601 |
| 2023/0023074 A1 | 1/2023 | Griffin |

* cited by examiner

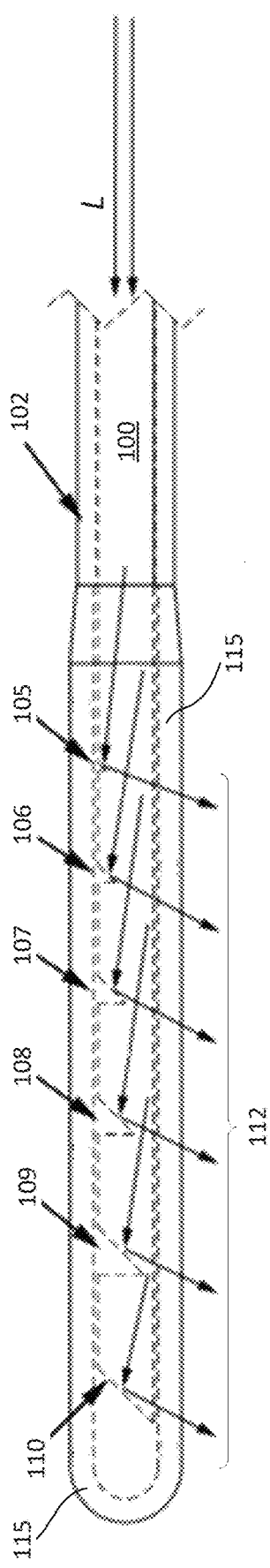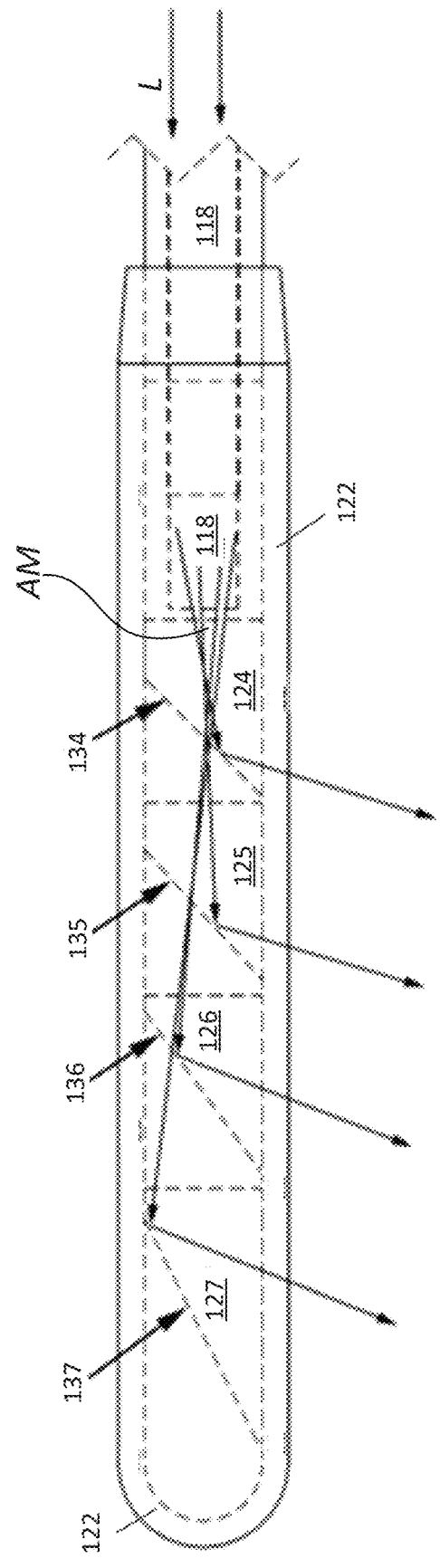
FIG. 1A (PRIOR ART)
FIG. 1B (PRIOR ART)

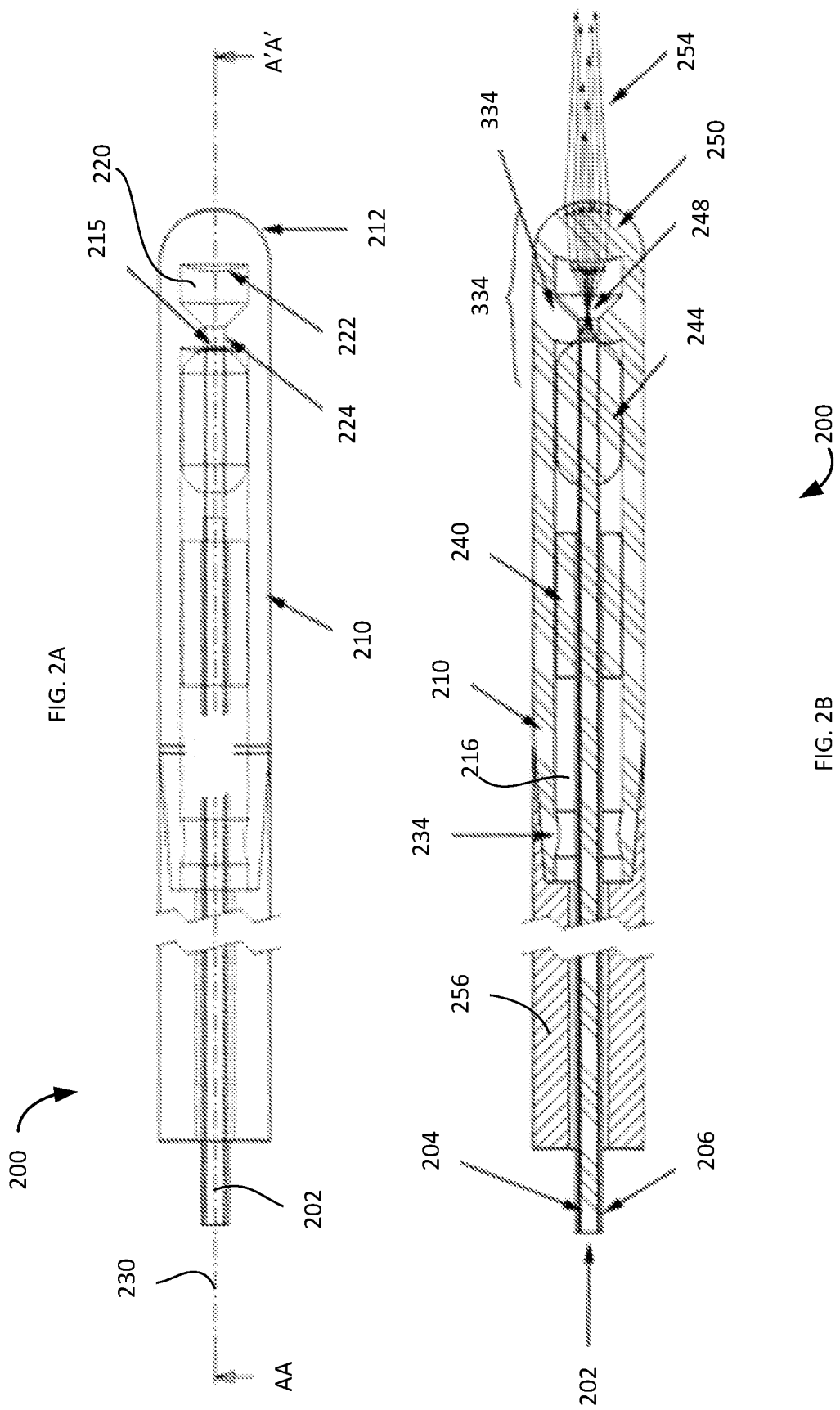

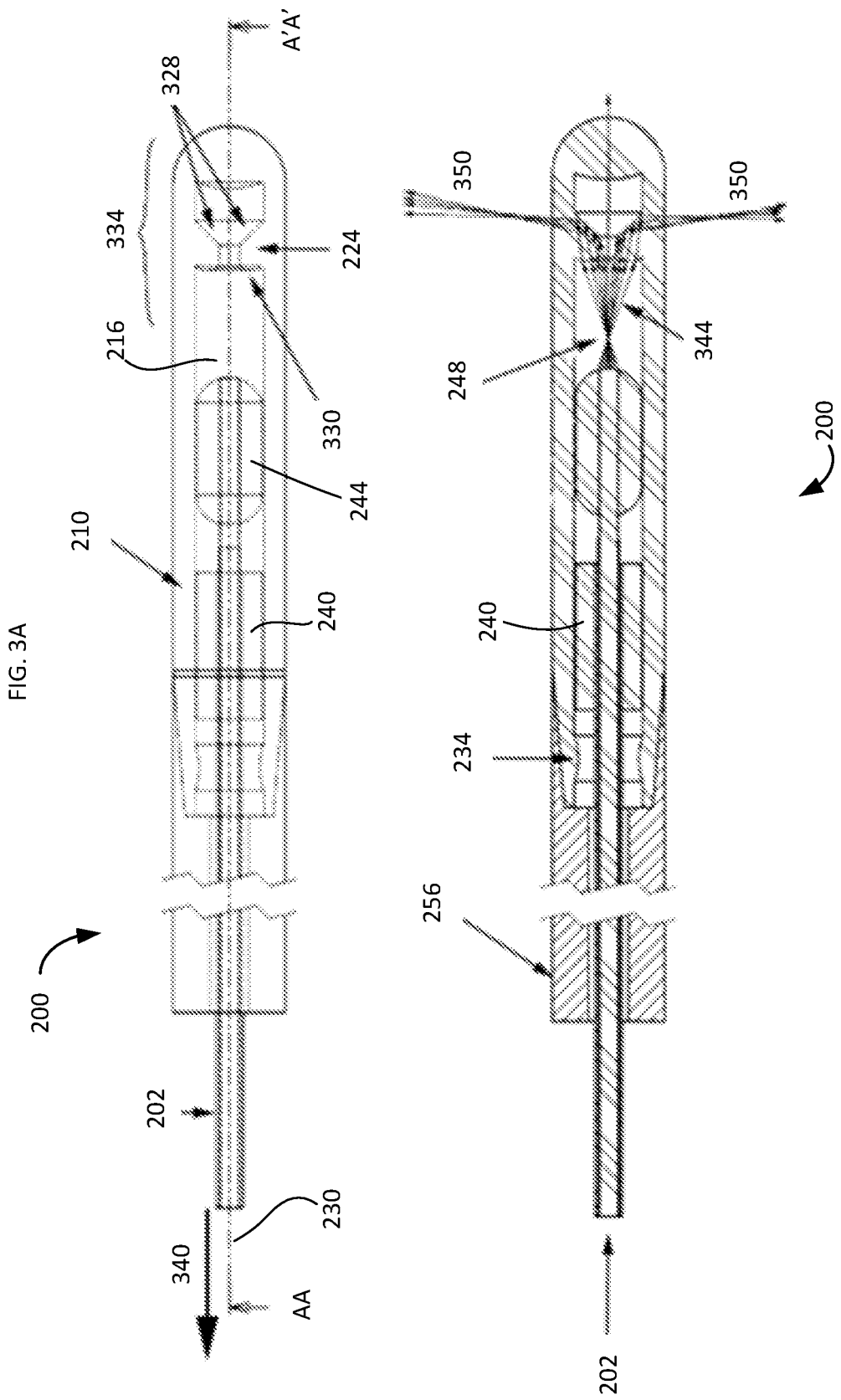

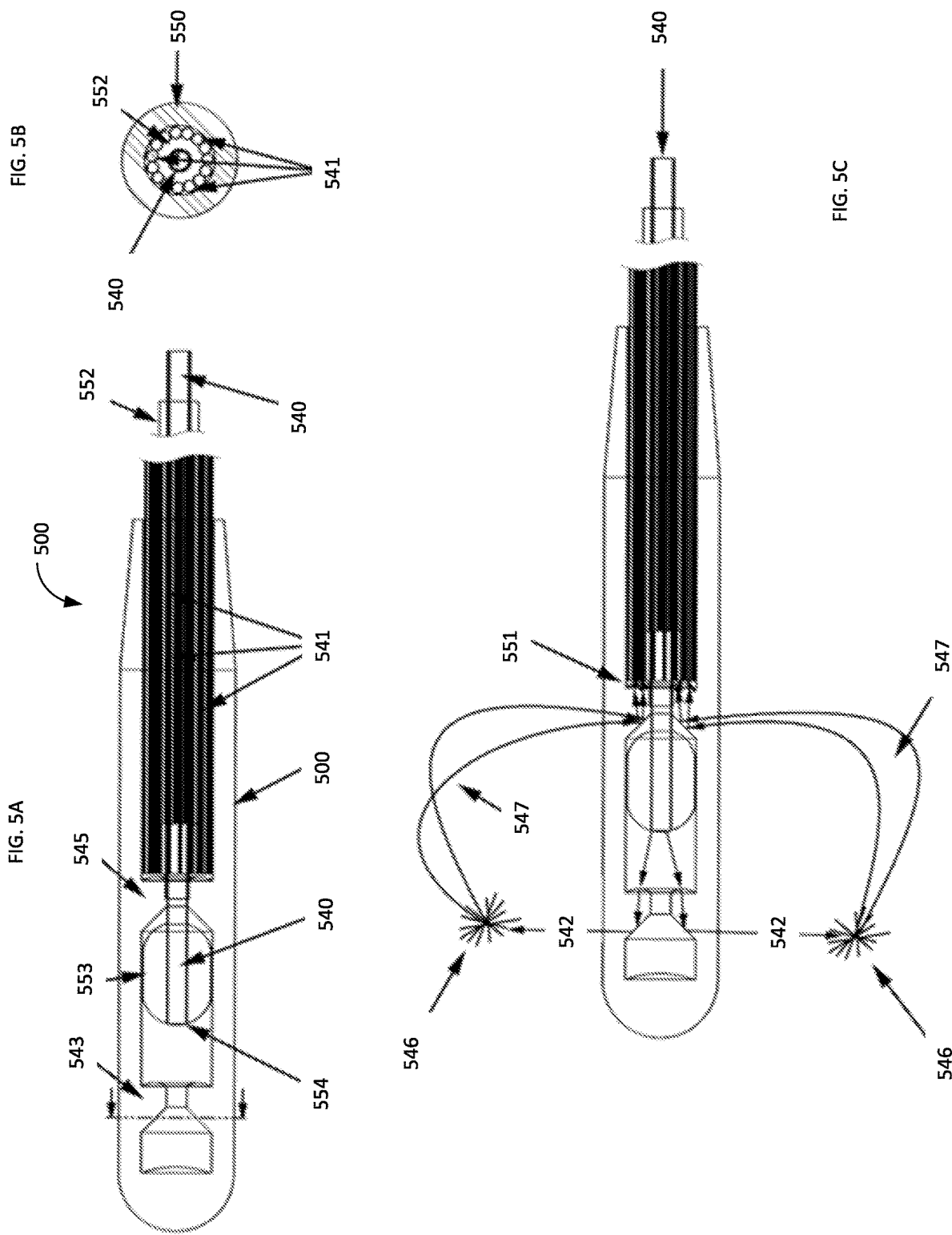

OPTICAL FIBER DEVICE WITH SPATIALLY SELECTABLE OUTPUT

CROSS-REFERENCE TO RELATED APPLICATIONS

This US Patent Application claims priority from and benefit of the U.S. Provisional Patent Application No. 63,425,472 filed on Nov. 15, 2022. This US Patent Application is also a continuation-in-part of the U.S. patent application Ser. No. 18/242,960 filed on Sep. 6, 2023, which claims priority from the U.S. Provisional Patent Application No. 63/414,974 filed on Oct. 11, 2022 and which is a continuation-in-part of the U.S. patent application Ser. No. 18/228,983 filed on Aug. 1, 2023. The U.S. patent application Ser. No. 18/228,983 claims priority from the U.S. Provisional Patent Application No. 63/405,984 filed on Sep. 13, 2022. The disclosure of each of the above-identified patent applications is incorporated by reference herein.

TECHNICAL FIELD

This invention relates to methodology(ies) for modification of spatial distribution of light exiting a piece of fiber optics (~a modification of a fiber-optic output light profile) configured to make the results of such modification to be useful in the treatment of various intracorporeal disease states with intense light (e.g., lasers), particularly endovenous and peripheral artery diseases.

RELATED ART

Fiber optical device configured to produce light output referred to as lateral light emission, radial light emission, and diffused light output are utilized in a variety of light-based surgical procedures (which include laser interstitial thermal therapy, endovenous laser ablation, endometrial coagulation, endovenous laser therapy, and photodynamic therapy, to name just a few). Typically, such fiber optical devices include a contraption structured to modify a conventional, along-the-axis light output from an optical fiber. Additional practical surgical interventions that may benefit from the employment of such modified output fibers include ablation, vaporization, and/or coagulation of tissues among which are hyperplastic prostate tissue, laryngeal tumors, and atherosclerotic and vulnerable plaques.

Modifications to optical fibers typically utilize the formation or addition of light-scattering elements to produce diffuse optical energy emission over significant lengths of fiber, including additions to an optical fiber structure for altering the axially-directed output (at distal termini) in both rigid and flexible designs. Fiber optics configured to effectuate light scatter are generally very limited in total power handling capacity due to conversion of a significant portion of the photonic energy channeled by an optical fiber to thermal energy, and due to a broad reliance upon polymer matrices for hosting/carrying the light scattering centers. These scattering modalities are generally referred to herein as diffuse (or diffusing) output fibers (or fiber optics, FO).

"Radial emission" has been typically used in related art to describe a fiber's light output ranging from that having standard divergence from a high numerical aperture (NA) fiber with simple flat polished (axial) output to that utilizing light reflected at and refracted by conical output surfaces. Broadly defined, these "radial output fibers" do produce a radial component if the term "radial" includes any off-axis emission (i.e., any fiber output other than a truly collimated output has a "radial" component or components).

Alternatively, within the realm of coagulating fibers, the use of a term "lateral emission" fibers (or, "laterally-emitting" fibers) is typically limited to denote those that produce multi-point, off-axis emissions, which are often highly distorted by Fresnel and total internal reflections produced by various employed light-redirecting optical mechanisms. One example of a laterally-emitting fiber optics includes, as shown schematically in FIG. 1A, an optical fiber 100 that is terminally (at an end thereof) stripped of a fiber cladding 102 and equipped with a series of progressively deeper notch cuts 105, 106, 107,108, 109, 110 on one side of the glass body of the fiber to reflect portions of the light L propagating within/channeled by the fiber off the fiber longitudinal axis (not shown), which portions of light 112 exit through a protective quartz cap 115 with which the output end of the fiber is equipped. Clearly, practical implementation of the notches on the glass body of the optical fiber remains at least involved and complicated. An equally impractical example illustrated in FIG. 1B from the same period utilized an axial emission fiber 118 that terminated into a cap structure 122 similar to structure 115 of FIG. 1A but that was complemented with stacked segments of cladded fiber disposed axially within the hollow of the protective cap 122. These segments 124, 125, 126, and 127 had corresponding distal reflective surfaces (typically—planar surfaces) 134, 135, 136, and 137 that were tilted at difference angles with respect to the axis of the cap 122—starting with one chosen to reflect a fraction of the angular modes of light AM present in the output OP from the distal facet of the fiber 118 and progressing in stages to such an angle that was substantially equal to the critical angle for total internal reflection as calculated for all angular modes carried within the fiber 118.

Other solutions provided by related art include simple high NA fibers with normal, axial type emission and cone tipped fiber (typically a mechanically polished cone or a frustoconical tip on either the high NA a the low NA fiber), whether bare—as schematically illustrated in FIG. 1C—or juxtaposed with a protective cap, FIG. 1D. FIG. 1C illustrates the optical fiber having the glass body 144 with a protective polymeric cladding 146, with the stripped-of-the-cladding 146 distal end of which the extension 140 is juxtaposed (for example, fused) that carries a conical tip causing the laterally-directed emission 150. FIG. 1D illustrates the contraption of FIG. 1C equipped with the protective cap 152.

The ideas of the broadest surgical application of the above-identified optical fiber devices differ in related art, giving rise to different applications of varicose vein surgery or endovenous laser treatment (EVLT) and endovenous laser ablation (EVLA). In both applications laser energy is used to preferentially damage (coagulate) varicose vessels for postsurgical absorption.

The EVLT camp advocates indirect heating of veins (via heating the blood within the vein, often to the point of boiling) by firing laser energy into the blood-filled vessel while moving the fiber along the length of the segment under treatment. If the fiber element is maintained within the center of the vessel, the radiant output from the fiber is relatively uniform and the speed of movement of the fiber element along the vessel is appropriately adjusted such as to account to variations in vessel diameter and shape; this approach is believed to result in minimization of complications of overtreatment such as vascular perforation, but at the same time not causing considerable thrombosis (blood clotting). EVLT is often performed with a simple, high numerical aperture (NA) and flat polished fiber, with a mechanism for preventing fiber tip to vessel wall contact.

The EVLA camp advocates heating the vessel wall directly, replacing the blood that normally populates the vessel with saline, thereby avoiding interactions with the blood to prevent post-operative complications from excessive thrombosis. EVLA typically utilized cone-tipped fibers like those depicted in FIGS. 1C and 1D and it is this latter camp for which uniform and true radially-shaped emission is most beneficial, as vessel perforations are most likely to result from direct but irregular application of laser energy.

Current laser therapies for peripheral arterial disease (PAD) utilize all-silica fiber lightguides or liquid waveguides (the latter employing saturated salt solution in FEP tubing) bounded by silica windows configured to transmit the intense ultraviolet (UV) energy produced by excimer laser sources. It is well recognized that neither EVLT device nor the EVLA device provides capacity for optimum treatment of all peripheral artery stenosis conditions: the former being capable of passing total occlusions with limited enlargement possible while the latter cannot pass total occlusions but provided greater enlargement potential for partial occlusions. There remains a need, therefore, in providing a device with externally and intraoperatively selectable light output: primarily axial (as in currently-used EVLT fiber optic devices) or primarily radial (as seems to be the optimum for EVLA and PAD devices). It would be further novel and useful for related art to gain an ability to detect the bare arterial or venous wall when exposed via complete removal of the arterial occlusion, at least for some portion of the inner circumference of the vessel, as an indicator that the maximum possible opening has been achieved. It would additionally be useful for such a bare arterial wall detection methodology to enable an automatic powering the laser source down, thereby preventing collateral damage to the vessel and precluding initiation of a clotting reaction.

SUMMARY OF THE INVENTION

The common idea behind the embodiments of the invention presented below involves providing a contraption that employs a conventional axially-emitting optical fiber, the spatial distribution of light output from which is further modified with a specific optical element (interchangeably referred to herein as a radial-redirection optical element). This optical element is judiciously structured such as to maintain a cross-sectional dimension of the light output from the optical fiber at or below the value of a fiber core diameter in order to avoid redirection of the light output in a radial direction by such optical element when the output facet of the optical fiber is near this special optical element. At the same time, the structure of this optical element ensures that the spatially diverging axially-directed light output from the optical fiber necessarily encounters and interacts with the radial-redirection optical element when the fiber output facet is repositioned away from the radial-redirection optical element. By providing a remote mechanism for moving the fiber output surface/facet between such the near (proximal to the radial-redirection optical element) and separated (distal from the radial-redirection optical element) positions, e.g., by axially moving the optical fiber relative to the radial-redirection element, the user can select the device light output to be predominantly axially directed or predominantly radially (sideways) directed.

Embodiments of the invention provide an article of manufacture that includes a specifically-structured tubular body that has an axis, an open end, and a closed end, and an axial hollow fluidly connecting the open end with the closed end. The axial hollow includes several hollow portions, the first of which defines the open end and has a first internal diameter. The second hollow portion is at the closed end and has a second internal diameter, while an intermediate hollow portion fluidly connects the first and second hollow portions and extends between a first axial location and a second axial location (the first axial location is closer to the closed end than the second axial location). The intermediate hollow portion has an intermediate internal diameter that monotonically varies from a first intermediate value at the first axial location to a second intermediate value at a third axial location (the third axial location is between the first and second axial locations). In at least one implementation, the intermediate internal diameter is monotonically reducing in value from the first intermediate value to the second intermediate value and/or is linearly reducing in value from the first intermediate value to the second intermediate value and/or is substantially constant between the second and third axial locations. In at least one embodiment, the first hollow portion is axially terminated at (or axially limited by) at a curved annular surface transverse to the axis. (When this is the case, the curved annular surface can be made convex as seen from the open end and/or at least a portion of the article between the curved annular surface and an outer surface of the article at the closed end is preferably made of an optically transparent material.) Alternatively or in addition, and substantially in every implementation, the outer surface of the article may be configured to be substantially cylindrical at least between the first and third axial locations; and/or the closed end of the article may be configured as an optical lens that has one or more of a curved outer surface and a curved surface that terminates the second hollow. Alternatively or in addition, and substantially in every implementation of the article, the first internal diameter and the second internal diameter can be dimensioned to be substantially equal to one another. In at least one specific case, the first hollow portion is a cylindrical hollow portion; and/or the article itself can be configured to be substantially axially-symmetric about the axis. Optionally, in substantially every implementation of the article, the tubular body may be complemented with and affixed to a cannula at the open end. Optionally, in substantially every implementation, the article may additionally include a lightguide having an output end and an output facet at the output end and disposed within the first hollow portion to have the output facet repositionally movable along the axis between a distal axial position substantially coinciding with the second axial position and a proximal axial position that is closer to the open end than the second axial position (in one specific case, such lightguide can be configured as an optical fiber). When this is the case, the lightguide may be structured to include a distal bulbous element at the output end of the lightguide (which distal bulbous element is preferably cross-sectionally dimensioned to slide smoothly within the first hollow portion while maintaining the output facet of the lightguide on the axis when the lightguide is being repositionally moved along the axis). Here, if and when the first hollow portion is axially terminated at a curved annular surface transverse to the axis and if when a front surface of the distal bulbous element is substantially in contact with said curved annular surface, the output facet of the lightguide is transversely (radially) substantially aligned with the intermediate hollow portion. At least one of the output facet of the lightguide and the front surface of the distal bulbous element can be formatted as a surface having non-zero curvature. Alternatively or in addition, the output facet of the lightguide and the front surface of the distal bulbous element can be dimensioned to merge with one another in a tangentially-parallel manner. Optionally, when the article includes a lightguide, the lightguide may be complemented with a proximal bulbous element at the lightguide (when this is the case, the proximal bulbous element is spatially separated from the distal bulbous element such that, when the output facet of the lightguide is in the proximal axial position, the proximal bulbous element is in contact with a structural element inside the first hollow portion while being prevented to move further towards the open end of the tubular body.

Optionally, when the article includes a lightguide (for example, an optical fiber), such optical fiber may be complemented with a fiber-optic controller that has a handle and a nose cap. A handle may have a handle axis and a handle hollow that is defined throughout the handle along the handle axis. The handle may include a collet with petals that extend along the handle axis and that have respectively-corresponding free distal ends and proximal ends (here, inner surfaces of the petals can be structured to be separated from the first axis at locations of the free distal ends by a first distance and to be separated from the first axis at locations of the proximal ends by a second distance smaller than the first distance). The nose cap may have a nose cap axis and a nose cap hollow defined throughout the nose cap and extending along the nose cap axis. (Here, a portion of the nose cap hollow may be structured as a cavity extending along the nose cap axis and dimensioned such that when the handle and the nose cap are mated by inserting the free distal ends into the cavity and snapping a ridge of a first surface into a notch on a second surface, the free distal ends are brought towards one another to change the first distance to become substantially equal to the second distance. The first surface is one of an inner surface of the cavity and an outer surface of the handle while the second surface is the other of the inner surface of the cavity and the other surface of the handle.)

Embodiments of the invention additionally provide a method for propagating light through the embodiment of the article of manufacture that incorporates a lightguide (as specified above). Such method includes at least one of the following processes: (i) when the output facet of the lightguide of such article of manufacture is in a first position on the axis: focusing light that is outcoupled from the output facet substantially at an axial location within the intermediate hollow portion, and propagating such light through the intermediate hollow portion, the second hollow portion, and the closed end thereby forming a first light output substantially axially directed outwardly from said article of manufacture while substantially not forming a second beam of light directed through a wall of said article transversely to the axis; and (ii) when the output facet of such article of manufacture is in a second position on the axis: focusing the light at an axial location within the first hollow portion, and totally internally reflecting a majority of the light at a surface having the intermediate internal diameter thereby forming a second light output, from the article of manufacture, that contains such majority of light and is directed transversely with respect to the axis. The method may additionally include the steps of reversibly repositioning the output facet of the lightguide between the first position on the axis and the second position on the axis while maintaining the output end of the waveguide oriented substantially axially. (The process of reversible repositioning may include preventing the lightguide from being moved closer to the open end of the tubular body of the article of manufacture once the output facet is placed to the second position of the axis.) The step of propagating the light through the closed end may include propagating the light through an optical lens element having positive optical power.

Embodiments of the invention further provide an optical switch. Such optical switch includes an optical termination element (optionally built as a one-piece construction) that has a tubular body with and axis, an open, and a closed end and that has an axially-symmetric internal surface with a diameter varying along the axis. The optical switch additionally includes an optical fiber passing into a hollow of the tubular through the open end disposed along the axis, an output facet of the optical fiber being repositionably movable within the hollow between a proximal axial position and a distal axial position while remaining secured therein such as to prevent the output facet from being removed from the open end and reaching said axially-symmetric internal surface. The optical switch is judiciously structured such as (a) when the output facet is in the distal axial position, to form an axially-directed beam of light by focusing light propagating through the optical fiber at a first location within the hollow and transmitting said light through the closed end; and such as (b) when the output faces is in the proximal axial position, to form light output containing a majority of said light propagating through the optical fiber and directed transversely with respect to the axis by focusing the light at a second location within the hollow and totally-internally reflecting the majority of said light at the axially-symmetric internal surface.

Embodiments of the invention additionally provide a method for changing a direction of propagation of light. The method includes redirecting a portion of light from a first light output (which exits an output facet of an optical fiber disposed along an axis of a tubular element having an open end and a closed end and which is directed axially and outwardly through the closed end and that further traverses the closed end of the tubular element) to a second light output that is directed transversely to the axis—by moving a focal point, to which said first light output converges after the existing the optical facet, away from the closed end. The method additionally includes at least partially totally internally reflecting said portion of light at a reflecting surface disposed at a radial distance from the axis (here, the radial distance varies along the axis). A method may additionally include a step of at least partially transmitting such portion of light through an annular curved surface prior to totally internally reflecting of light. In at least one implementation, the process of moving a focal point may include moving the focal point from a distal axial location within an intermediate hollow of the tubular element to a proximal axial location within a first hollow of the tubular element (here, the first hollow and the intermediate hollow are fluidly connected with one another and a transverse dimension of the intermediate hollow is smaller than the transverse dimension of the first hollow). Alternatively or in addition, and in at least one implementation of the method, the process of moving a focal point may include maintaining an orientation of the optical fiber within the tubular element to be along the axis while maintaining a position of the output facet of the optical fiber within the tubular element to be at the axis. Alternatively or in addition, and at least in one embodiment, the method may also include redirecting such portion of light in reverse—that is, from the second light output to the first light output—by repositioning the focal point towards the closed end to substantially completely cease the second light output. (In the latter case, the process of so-repositioning may include maintaining an orientation of the optical fiber within the tubular element to be along the axis while maintaining a position of the output facet of the optical fiber within the tubular element to be at the axis. Further, in more that one embodiment, any of the process of moving and the process of repositioning may be configured to include axially translating a bulbous element, affixed to the optical fiber at an end thereof, within a hollow of the tubular element (here, a front surface of the bulbous element facing the closed end and a surface of the output facet of the optical fiber are merging with one another in a tangentially-parallel fashion). The process of translating may be configured to position the front surface of the bulbous element in contact with an annular curved surface and/or to separate the front surface of the bulbous element from being in contact with the annular curved surface (where the annular curved surface is located between the open and the reflecting surface as seen along the axis).

Alternatively or in addition, and substantially in every implementation of the method, the step of redirecting may include transmitting at least a portion of light exiting the output facet through a lens element limited by an output surface of the closed end and an inner surface of the closed end, and/or transmitting the at least a portion of light through the inner surface that is convex as seen from the open end. The process if at least partially totally internally reflecting generally includes, in an embodiment, (i) at least partially totally internally reflecting light at the reflecting surface having a first cross-sectional diameter at a first axial location and a second cross-sectional diameter at a second axial location (the first axial location being closer to the open end than the second axial location and the first cross-sectional diameter being smaller than the second cross-sectional diameter) and/or (ii) at least partially totally internally reflecting light at the reflecting surface a cross-sectional diameter of which is monotonically changing along the axis.

BRIEF DESCRIPTION OF THE DRAWINGS

For a more complete understanding of the disclosure, reference should be made to the following detailed description and accompanying drawing figures wherein:

FIGS. 1A, 1B, 1C, and 1D schematically depict prior art radially-emitting optical fiber devices configured for EVLT.

FIGS. 2A and 2B illustrate an embodiment of the optical fiber device in a state in which the emission from the device is predominantly axially-directed (the optical fiber in in an "axial emission position").

FIGS. 3A and 3B illustrate the embodiment of FIGS. 2A, 2B in a state in which the emission from the device is predominantly radially-directed (the optical fiber component of the device is in a "radial emission position").

FIGS. 5A, 5B, 5C depict a related embodiment of the invention.

Figure 1C:
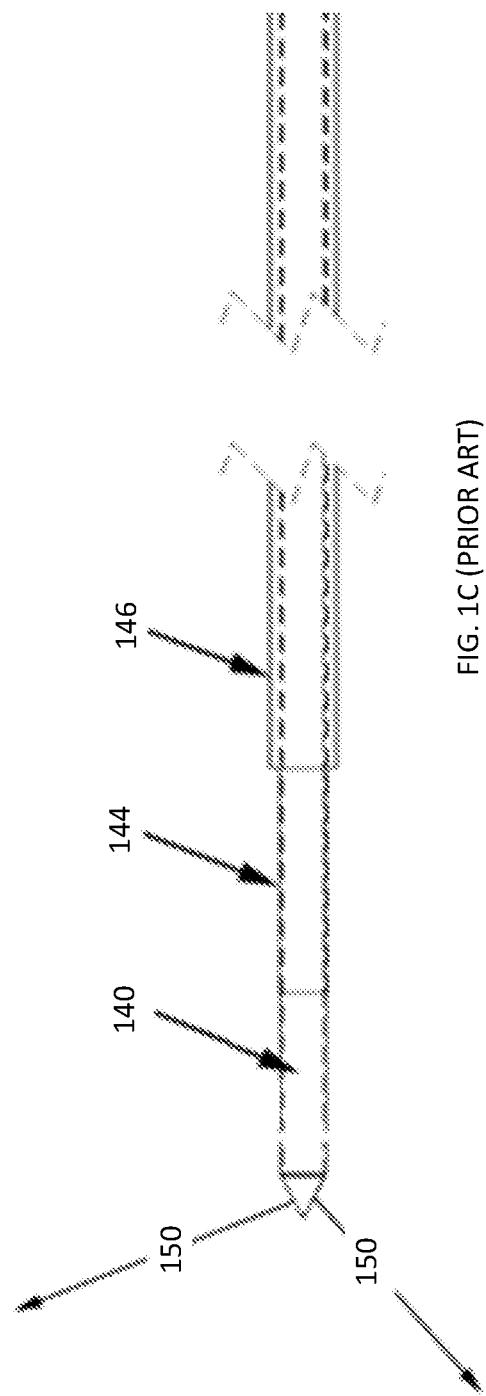
Figure 1D:
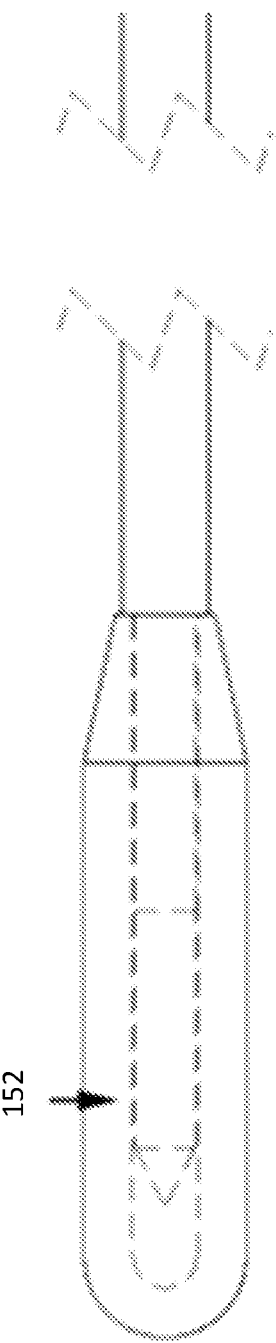

While specific embodiments are illustrated in the Figures, with the understanding that the disclosure is intended to be illustrative, these embodiments are not intended to limit the invention described and illustrated herein.

Generally, the sizes and relative scales of elements in Drawings may be set to be different from actual ones to appropriately facilitate simplicity, clarity, and understanding of the Drawings. For the same reason, not all elements present in one Drawing may necessarily be shown in another. While specific embodiments are illustrated in the figures with the understanding that the disclosure is intended to be illustrative, these specific embodiments are not intended to limit the scope of invention implementations of which are described and illustrated herein.

DETAILED DESCRIPTION

Features, purposes, and advantages of embodiments of the present invention will become apparent from the following detailed description. It should be understood, however, that the detailed description and the presented specific examples are given by way of illustration only, and various changes and modifications within the spirit and scope of the invention will become apparent to those skilled in the art from this detailed description.

The term "fiber optic termination" (or termination for an optical fiber, OF) is typically used in related art to designate a construction configured to connect the optical fiber to an external device and/or to spatially configure the distribution of a light-wave exiting the optical fiber in a desired fashion.

Multipurpose terminations for a single optical fiber have been used in related art to alternate between vaporization modes and cauterization modes for, for example, side-fire fiber terminations as depicted in FIG. 19 of U.S. Pat. No. 9,488,782. The operation of such systems relies on the altering of the effective focal length of a micro-optical element (that is typically structured to be a part of the termination of the OF) through control of the filling for affecting the divergence of emanating light in a single direction. In stark contradistinction with the related art, embodiment of the present invention are configured to depend at least in part on the axial movement of the optical fiber within the termination element while substantially preserving the degree of divergence of light that emanates from the output facet of the fiber—as seen along the optical axis of the fiber—while substantially evading the process of redirection in the off-axis direction (away from the op[tical axis) substantially entirely in one position of the optical fiber and engaging the dedicated element of the optical termination (which is responsible for such redirection of light propagation off-axis) form an off-axis beam of light in another position of the optical fiber. Therefore, an embodiment of the optical-fiber device of the present invention is configured to operate as an optical switch that delivers at least the majority of light (if not substantially all light) emanating from the output facet 215 of the optical fiber in an axial direction in one state of the switch and in an off-axis direction in another state of the switch. A skilled artisan will readily appreciate that the direction of the optical emission from an embodiment of the device is changes to effectuate vaporization of the target material or tissue in an axial direction (which, in the specific case of the peripheral arterial disease, PAD, corresponds to passing the occlusion) to that in a substantially radial direction (or in an off-axis direction, which in the case of PAD corresponds to the process of clearing the occlusion by widening an opening in a blood vessel).

To this end, an embodiment of the device 200 of the invention is schematically depicted in FIGS. 2A, 2B, 3A, and 3B, and FIGS. 4A through 4J are used to describe a step-by-step process of assembly of the embodiment 200 as well as the functions of its essential components. In that, FIGS. 2B and 3B provide cross-sectional views (taken along the plane labelled as AA-A'A') of the gadget presented in FIGS. 2A, 3A respectively, to clearly demonstrate the two states of positioning of the optical fiber component within the termination element. In reference to FIGS. 2A through 3B, the distal portion of the optical fiber 202 (which has an inner typically silica-based, core 204 surrounded with a preferably fluorine-doped silica cladding 206) is affixed within the optical termination element 210, configured as a protective quartz-based capsule. Optionally, the element 210 is a one-piece construction. The optical termination element 210 is configured to have a generally tubularly-shaped body with an open end (through which the optical fiber 202 is inserted in the process of assembly of the embodiment 200) and a closed (and/or sealed) end labelled as 212. The open and closed ends of the capsule 210 are fluidly connected through the inner hollow of the capsule, which hollow includes a first hollow portion 216 (starting near and substantially defining the open end) that has a first internal diameter, a second hollow portion 220 (near the closed end) having a second internal diameter, and an intermediate hollow portion 224 between the first and second hollow portions.

The second hollow portion 220 may be terminated with a spatially curved surface 222 (in one specific case configured as a surface of a lens element possessing positive optical power). The intermediate hollow portion extends between a first axial location (at which the intermediate hollow portion merges with the second hollow portion) and a second axial location (at which the intermediate hollow portion merges with the first hollow portion) and has an intermediate internal diameter that monotonically varies from a first intermediate value at the first axial location to a second intermediate value at a third axial location that is defined between the first and second axial locations.

In at least one specific case, the intermediate internal diameter of the intermediate hollow portion of the hollow of the optical fiber termination is monotonically reducing from the first intermediate value to the second intermediate value and/or is linearly reducing from the first intermediate value to the second intermediate value and/or is substantially constant between the second and third axial locations. As a result of so structuring the hollow of the optical termination element 201, the intermediate hollow portion defines the substantially conical axially-symmetric surface 328 (seen in FIG. 3A). In the vicinity (or even at) the second axial location, where the first hollow portion and the intermediate hollow portion are merging, the first hollow portion may be axially terminated at (or axially limited by) a curved annular surface shown as 330 in FIG. 3A that is transverse to the axis 230 of the embodiment 200 of the optical fiber-based device and that forms an annularly-shaped lens element. A skilled artisan will readily appreciate that a portion of the optical fiber termination element corresponding to the surface 220, the intermediate hollow portion 224, and the surface 328 can be viewed as a light-redirecting element 334, as discussed in more detail below)

The first internal diameter of the first hollow portion 216 may be optionally restricted, in a limited axial region of the first hollow portion, to a smaller value to form and internal restriction region 234. When the optical fiber element 202 carries at least one of the two quartz elements shown as a proximal element 240 and a distal element 244 (each of which may be fused with and onto the glass/quartz body of the optical fiber), the internal restriction region provides a failsafe stop for the spatially limited axial movement of the fiber outwards of the open end of the optical termination 210, while the bulbous distal element 244 is configured as a forward travel stop element to limit the axial repositioning of the output facet 215 of the optical fiber towards the closed end of the optical termination 210.

As shown in FIGS. 2A through 3B, the distal (facing the closed end of the optical termination 210) end of the element 244 may be spatially curved (optionally—polished together with the output facet of the optical fiber) to form a lens surface which changes a degree of spatial divergence of light channeled by the optical fiber 202 into the terminal element 210 for form the emission that is somewhat focused to produce a focal spot 248.

Referring now specifically to FIGS. 2A, 2B, the optical fiber-based device 200 is shown in a state in which the output facet of the optical fiber 202 is located substantially at or in the vicinity of the second axial location (such that the curved surface 330 and the distal end of the bulbous distal element 244 are substantially in contact with one another). In this position (which signifies the state of the device 200 in which the light output from the output facet of the fiber 202 is directed substantially axially while missing/avoiding an interaction with the quasi-conical surface 328), the focal spot 118 is formed somewhere within the intermediate hollow portion 224, thereby passing through the bore 224 of the light-redirecting element 334. The light emission out of the fiber then axially imparts the lens-surface element 222 and, as a result of interaction with this surface 222, has its degree of spatial divergence reduced (thereby, for example, propagating towards the outer surface of the closed end 212 as a quasi-collimated beam 250). Depending on the chosen shape of the outer surface of the closed end 212, the spatial degree of collimation of the beam 250 can be further refined towards the desired value, and be either slightly focused or substantially-fully collimated, 254, in a non-limiting example. The radiative output 254 then can be used for burning a chosen target—in one case, for vaporizing a through hole within an atherosclerotic plaque, for example.

FIGS. 3A, 3B, on the other hand, depict the structure 200 in a state in which the output facet of the op[tical fiber 202 is axially removed (separated) from the surface curved surface 330 (optionally, up to a point when the axial movement of the proximal end 240 fused with the body of the optical fiber 202 is restricted by the failsafe stop 234. Here, the fiber 202 is shown to have been axially repositioned within the first hollow portion 216 along the arrow 340 such that the light emission focal spot 248 is now located well before the light-redirecting element 334. As a result, the bulk of the emission 344 imparts the input curved surface 330 of the redirecting element 334 (rather than passing through the intermediate hollow portion) to be redirected towards the quasi-conical surface 328 and, upon being reflected internally at the surface 328 according to Snell's law, forms the predominantly off-axis (radially) directed emission 350. Movement of the fiber 202 relative to the fused quartz capsule (cap) 210 may be accomplished, in one specific implementation, via an indexing mechanism placed outside the body during surgery (not shown) with relative motion communicated via the protective tube/sheath housing the fiber 202. Overall, the skilled artisan will now appreciate that embodiments of the invention include an article of manufacture configured as a specifically dimensioned optical fiber termination element as well as the optical-fiber-based device including such optical fiber termination element and a lightguide (optical fiber being one example) contains a distal bulbous element at the output end of the lightguide. Such distal bulbous element is cross-sectionally dimensioned to slide smoothly within the first hollow portion of the optical termination element while maintaining the output facet of the lightguide on the axis when the lightguide is being repositionally moved along the axis. The lightguide may further include an (optionally bulbous) proximal element separated from the distal bulbous element such that, when the output facet of the lightguide is in the proximal axial position, the proximal bulbous element is in contact with a structural element inside the first hollow portion while being prevented to move further towards the open end of the tubular body.

An embodiment of the device discussed above is, understandably, structured to effectuate a method for propagating light. Such method includes a first combination of steps of focusing light (that is outcoupled from the output facet of the lightguide of the device when the output facet of the lightguide is in a first position on the axis) substantially at an axial location within the intermediate hollow portion, and propagating such light through the intermediate hollow portion, the second hollow portion, and the closed end thereby forming a first light output substantially axially directed outwardly from the device while substantially not forming a second beam of light directed through a wall of said article transversely to the axis. Alternatively or in addition, the method may include a second combination of steps of focusing such light at an axial location within the first hollow portion (when the output facet is in a second position on the axis) and then totally internally reflecting a majority of such light at a surface having the intermediate internal diameter thereby forming a second light output from the device that contains such majority of light and that is directed transversely with respect to the axis.

Figure 4J:
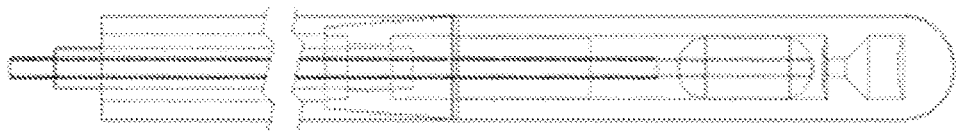
FIGS. 4A, 4B, 4C, 4D, 4E, 4F, 4G, 4H, 4I, and 4J illustrate steps involved in forming/assembling/producing the embodiment of FIGS. 2A, 2B, 3A, 3B.
Figure 4I:
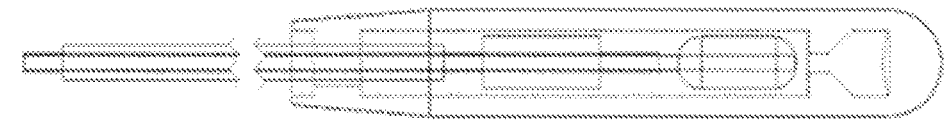
Figure 4H:
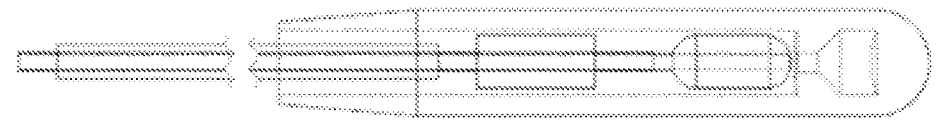
Figure 4G:
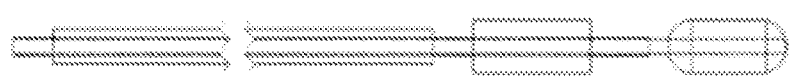
Figure 4F:
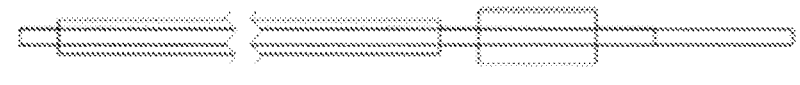
Figure 4E:
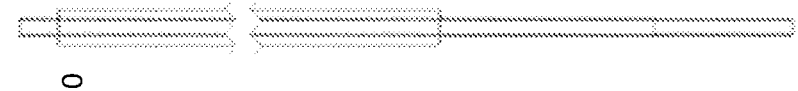
Figure 4D:
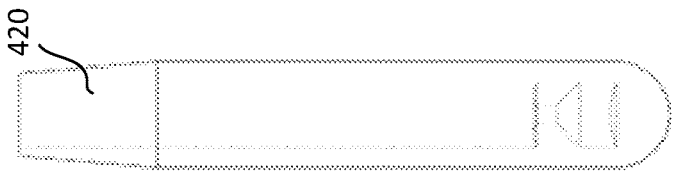
Figure 4C:
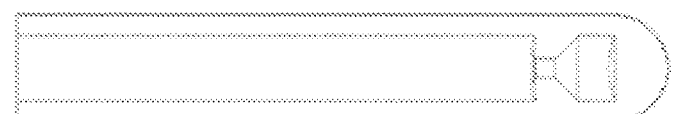
Figure 4B:
Figure 4A:
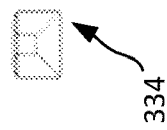

FIGS. 4A, 4B, 4C, 4D, 4E, 4F, 4G, 4H, 4I, 4J depict the step-by-step assembly stages for producing the embodiment of the optical fiber-based device 200 discussed above. FIG. 4A depicts an annular lens 330 and redirection element 334 containing such lens made from a short section of fused quartz tubing where the upper side (input surface) is rounded, forming an annular lens similar to a simple fire-polished tube end and the bottom opening is chamfered at the critical angle for total internal reflection of the worst-case ray that will be presented by the fiber emission divergence as affected by the annular lens. FIG. 4B illustrates a situation in which a longer quartz tube 410 is positioned over the element 334 and the adjacent wall of the tube is heated until the two elements fuse. The distal end of the larger tube 410 is then sealed, FIG. 4C, with slight excess glass provided to produce the lens referenced as 222 in FIG. 2A. IN a specific case, the cap proximal end is chamfered, FIG. 4D, for mating with the motion communicating and protective tube 210 in FIG. 3B.

The fiber optic is prepared by stripping off the polymer coating and buffer, FIG. 4E, such that a short section of glass tubing may be glued onto the bare coating as in FIG. 4F and in FIG. 4G a fused quartz tube with rounded edges may be fused onto the bare glass and laser formed into an output lens 215 as discussed above for element 244, FIGS. 2A, 2B. The prepared fiber is positioned within the chamfered quartz capsule 420 of FIG. 4D (see FIG. 4H and the restriction 234 in FIG. 2B and FIG. 3B for the stop element 240 in FIG. 2B is formed or glued in place. Finally, the protective tube (cannula) 256 in FIG. 2B and FIG. 3B is secured to the quartz capsule (tubular element) 410 with adhesive to provide communication of relative motion. In at least one specific implementation, the cannular can be structured substantially similarly to that disclosed in the U.S. patent application Ser. No. 18/242,960.

Additional related embodiments can be envisioned, in which the light-redirecting element can be configured to redirect light radially rather than annularly (as element 334 does) and in which the conical TIR surface is positive and frustoconical instead of negative and hollow (as in the embodiment 200), but such variations may result in Fresnel reflection losses of light that are greater than those characterizing the embodiment 200. Another related embodiment 500 is schematically illustrated in FIGS. 5A, 5B, and 5C. Here, the transparent (fused quartz, fused silica, sapphire) capsule (termination element) 550 contains two TIR conical/annular TIR elements 543 and 554 whereby diffuse reflected light 547 (or perhaps even fluorescent emission 546) from the tissue under radial emission 542 excitation may be gathered by a second conical TIR element 545 placed over the emission/excitation fiber 540 and proximal to the distal stop element 553 (containing the beam shaping lens 554) for coupling 551 to a ring of fibers 541 that is arranged about the emission fiber 540 for the purpose of monitoring the tissue condition. Such a secondary TIR element 545 for gathering the tissue spectral signature may be like the emission TIR element 143 or may be substantially altered for optimization of scattered light 547 recovery. Were such a diffuse reflectance or fluorescence signal recovered in this manner be capable of distinguishing healthy tissue, e.g., inner arterial wall, from plaque, the laser ablation action could be terminated by such detection thereby eliminating the risk of overtreatment and the consequent arterial damage.

It is appreciated that, when an embodiment of the article of manufacture discussed above includes an optical fiber—such as the optical fiber 540 (see embodiment 500) or optical fiber 202 (see embodiment 200)—there may be a fiber-optic controller added to the article of manufacture away from the tubular element and/or cannula, closer to or substantially at the proximal end of the optical fiber. The fiber controller in at least one case may be structured as discussed in the U.S. patent application Ser. No. 18/228,983, the disclosure of which is incorporated by reference herein. Alternatively, such fiber optic controller can be structured substantially analogously to that disclosed in reference to FIGS. 7A, 7B, 7C, and 7D of the U.S. patent application Ser. No. 18/242,960, the disclosure of which is incorporated by reference herein.

The disclosure of each of patent documents or other documents referred to in this application is incorporated herein by reference.

References throughout this specification to "one embodiment," "an embodiment," "a related embodiment," or similar language mean that a particular feature, structure, or characteristic described in connection with the referred to "embodiment" is included in at least one embodiment of the present invention. Thus, appearances of the phrases "in one embodiment," "in an embodiment," and similar language throughout this specification may, but do not necessarily, all refer to the same embodiment. It is to be understood that no portion of disclosure, taken on its own and in possible connection with a figure, is intended to provide a complete description of all features of the invention.

For the purposes of this disclosure and the appended claims, the use of the terms "substantially", "approximately", "about" and similar terms in reference to a descriptor of a value, element, property or characteristic at hand is intended to emphasize that the value, element, property, or characteristic referred to, while not necessarily being exactly as stated, would nevertheless be considered, for practical purposes, as stated by a person of skill in the art. These terms, as applied to a specified characteristic or quality descriptor means "mostly", "mainly", "considerably", "by and large", "essentially", "to great or significant extent", "largely but not necessarily wholly the same" such as to reasonably denote language of approximation and describe the specified characteristic or descriptor so that its scope would be understood by a person of ordinary skill in the art. In one specific case, the terms "approximately", "substantially", and "about", when used in reference to a numerical value, represent a range of plus or minus 20% with respect to the specified value, more preferably plus or minus 10%, even more preferably plus or minus 5%, most preferably plus or minus 2% with respect to the specified value. As a non-limiting example, two values being "substantially equal" to one another implies that the difference between the two values may be within the range of +/−20% of the value itself, preferably within the +/−10% range of the value itself, more preferably within the range of +/−5% of the value itself, and even more preferably within the range of +/−2% or less of the value itself. The use of these terms in describing a chosen characteristic or concept neither implies nor provides any basis for indefiniteness and for adding a numerical limitation to the specified characteristic or descriptor. As understood by a skilled artisan, the practical deviation of the exact value or characteristic of such value, element, or property from that stated falls and may vary within a numerical range defined by an experimental measurement error that is typical when using a measurement method accepted in the art for such purposes.

The use of these terms in describing a chosen characteristic or concept neither implies nor provides any basis for indefiniteness and for adding a numerical limitation to the specified characteristic or descriptor. As understood by a skilled artisan, the practical deviation of the exact value or characteristic of such value, element, or property from that stated falls and may vary within a numerical range defined by an experimental measurement error that is typical when using a measurement method accepted in the art for such purposes.

The term "A and/or B" or a similar term means "A alone, B alone, or A and B together" and is defined to be interchangeable with the term "at least one of A and B."

While the invention is described through the above-described exemplary embodiments, it will be understood by those of ordinary skill in the art that modifications to, and variations of, the illustrated embodiments may be made without departing from the inventive concepts disclosed herein. Disclosed aspects, or portions of these aspects, may be combined in ways not listed above. Accordingly, the invention should not be viewed as being limited to the disclosed embodiment(s).

The invention claimed is:

1. An article of manufacture comprising:
   a tubular body having an axis, an open end, and a closed end, and
   an axial hollow fluidly connecting the open end with the closed end,
   wherein the axial hollow includes
     a first hollow portion defining said open end and having a first internal diameter,
     a second hollow portion at the closed end and having a second internal diameter, and
     an intermediate hollow portion fluidly connecting the first and second hollow portions,
       wherein the intermediate hollow portion extends between a first axial location and a second axial location and having an intermediate internal diameter that monotonically varies from a first intermediate value at the first axial location to a second intermediate value at a third axial location,
     wherein the first axial location is closer to the closed end than the second axial location and the third axial location is between the first and second axial locations,
   and further comprising:
     a lightguide having an output end and an output facet at the output end and disposed within the first hollow portion to have the output facet repositionally movable along the axis between a distal axial position substantially coinciding with the second axial position and a proximal axial position that is closer to the open end than the second axial position.

2. An article of manufacture according to claim 1, wherein the intermediate internal diameter:
   (2A) is monotonically reducing from the first intermediate value to the second intermediate value; and/or
   (2B) is linearly reducing from the first intermediate value to the second intermediate value;
   and/or
   (2C) is substantially constant between the second and third axial locations.

3. An article of manufacture according to claim 1, wherein the first hollow portion is axially terminated at a curved annular surface transverse to the axis.

4. An article of manufacture according to claim 3, wherein at least a portion of the article between the curved annular surface and an outer surface of the article at the closed end is made of an optically transparent material.

5. An article of manufacture according to claim 3, wherein the curved annular surface is convex as seen from the open end.

6. An article of manufacture according to claim 1, wherein an outer surface of the article is substantially cylindrical at least between the first and third axial locations.

7. An article of manufacture according to claim 1, wherein the closed end is configured as an optical lens having one or more of a curved outer surface and a curved surface that terminates the second hollow.

8. An article of manufacture according to claim 1, wherein the first internal diameter and the second internal diameter are substantially equal to one another and/or wherein the first hollow portion is a cylindrical hollow portion.

9. An article of manufacture according to claim 1, that is substantially axially-symmetric about the axis and/or that further comprises a cannula affixed to the tubular body at the open end.

10. An article of manufacture according to claim 9, comprising a cannula-mount segment of a fiber-control device affixed to the cannula.

11. An article of manufacture according to claim 10, wherein the open end is dimensioned to receive an optical fiber along a tube axis, and further comprising the optical fiber cooperated with the fiber control device and inserted into the first hollow.

12. An article of manufacture according to claim 11, further comprising a centering sleeve disposed about an output tip of the optical fiber.

13. An article of manufacture according to claim 1, whether the lightguide contains a distal bulbous element at the output end of the lightguide,
   wherein the distal bulbous element is cross-sectionally dimensioned to slide smoothly within the first hollow portion while maintaining the output facet of the lightguide on the axis when the lightguide is being repositionally moved along the axis.

14. An article of manufacture according to claim 13, wherein, when the first hollow portion is axially terminated at a curved annular surface transverse to the axis and when a front surface of the distal bulbous element is substantially in contact with said curved annular surface, the output facet of the lightguide is transversely aligned with the intermediate hollow portion.

15. An article of manufacture according to claim 13, wherein at least one of the output facet of the lightguide and the front surface of the distal bulbous element is a surface having non-zero curvature.

16. An article of manufacture according to claim 13, further comprising a proximal bulbous element at the lightguide,
wherein the proximal bulbous element is separated from the distal bulbous element such that, when the output facet of the lightguide is in the proximal axial position, the proximal bulbous element is in contact with a structural element inside the first hollow portion while being prevented to move further towards the open end of the tubular body.

17. An article of manufacture according to claim 13, wherein the lightguide includes an optical fiber inserted into the first hollow and further comprising a fiber-control device affixed to the optical fiber.

18. An article of manufacture according to claim 17, wherein the fiber-control device includes:
(i) a handle having a handle axis and a handle hollow that is defined throughout the handle along the handle axis, the handle comprising a collet with petals that extend along the handle axis and that have respectively-corresponding free distal ends and proximal ends,
wherein inner surfaces of the petals are separated from the first axis at locations of the free distal ends by a first distance and inner surfaces of the petals are separated from the first axis at locations of the proximal ends by a second distance smaller than the first distance; and
(ii) a nose cap having a nose cap axis and a nose cap hollow defined throughout the nose cap and extending along the nose cap axis,
wherein a portion of the nose cap hollow is a cavity extending along the nose cap axis and dimensioned such that when the handle and the nose cap are mated by inserting the free distal ends into the cavity and snapping a ridge of a first surface into a notch on a second surface, the free distal ends are brought towards one another to change the first distance to become substantially equal to the second distance,
wherein the first surface is one of an inner surface of the cavity and an outer surface of the handle while the second surface is the other of the inner surface of the cavity and the other surface of the handle.

19. An article of manufacture according to claim 13, wherein the output facet of the lightguide and the front surface of the distal bulbous element are merging with one another in a tangentially-parallel manner.

20. A method comprising:
with the use of the article of manufacture according to claim 1, comprising a lightguide having an output end and an output facet at the output end and disposed within the first hollow portion to have the output facet repositionally movable along the axis between a distal axial position substantially coinciding with the second axial position and a proximal axial position that is closer to the open end than the second axial position, performing at least one of the following actions:
(19A) when the output facet of the lightguide of the article of manufacture is in a first position on the axis:
focusing light that is outcoupled from the output facet substantially at an axial location within the intermediate hollow portion, and
propagating said light through the intermediate hollow portion, the second hollow portion, and the closed end thereby forming a first light output substantially axially directed outwardly from said article of manufacture while substantially not forming a second beam of light directed through a wall of said article transversely to the axis;
and/or
(19B) when the output facet of the article of manufacture is in a second position on the axis:
focusing said light at an axial location within the first hollow portion, and
totally internally reflecting a majority of said light at a surface having the intermediate internal diameter thereby forming a second light output, from the article of manufacture, that contains said majority and is directed transversely with respect to the axis.

21. A method according to claim 20, comprising:
reversibly repositioning the output facet of the lightguide between the first position on the axis and the second position on the axis while maintaining the output end of the waveguide oriented substantially axially.

22. A method according to claim 21, wherein said reversibly repositioning includes preventing the lightguide from being moved closer to the open end of the tubular body of the article of manufacture once the output facet is placed to the second position of the axis.

23. A method according to claim 20, wherein said propagating the light through the closed end includes propagating the light through an optical lens element having positive optical power.

* * * * *